United States Patent
Jeannotte et al.

(10) Patent No.: US 9,989,459 B2
(45) Date of Patent: Jun. 5, 2018

(54) SYSTEMS AND METHODS FOR REFRACTIVE INDEX DETECTION

(71) Applicant: Waters Technologies Corporation, Milford, MA (US)

(72) Inventors: Anthony C. Jeannotte, Foxborough, MA (US); Mark Basile, Hollis, NH (US); Senthil Bala, Westborough, MA (US); Colin Fredette, Ashland, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 123 days.

(21) Appl. No.: 14/775,752

(22) PCT Filed: Mar. 11, 2014

(86) PCT No.: PCT/US2014/023142
§ 371 (c)(1),
(2) Date: Sep. 14, 2015

(87) PCT Pub. No.: WO2014/150396
PCT Pub. Date: Sep. 25, 2014

(65) Prior Publication Data
US 2016/0018326 A1    Jan. 21, 2016

Related U.S. Application Data

(60) Provisional application No. 61/819,811, filed on May 6, 2013, provisional application No. 61/789,098, filed on Mar. 15, 2013.

(51) Int. Cl.
*G01N 21/05* (2006.01)
*G01N 30/74* (2006.01)
*G01N 21/41* (2006.01)

(52) U.S. Cl.
CPC ......... *G01N 21/4133* (2013.01); *G01N 21/05* (2013.01); *G01N 30/74* (2013.01); *G01N 2021/4146* (2013.01)

(58) Field of Classification Search
None
See application file for complete search history.

(56) References Cited

U.S. PATENT DOCUMENTS 2,427,996 A * 9/1947 Seaman ............. G01N 21/4133
250/238
2,810,315 A * 10/1957 Miller ................ G01N 21/4133
250/576

(Continued)

FOREIGN PATENT DOCUMENTS

| GB | 1267589 A | 3/1972 |
|----|-----------|--------|
| WO | 2012148793 A1 | 11/2012 |
| WO | 2013025851 A1 | 2/2013 |

OTHER PUBLICATIONS

International Search Report in International Patent Application No. PCT/US14/23142, dated Jul. 30, 2014; 3 pages.

(Continued)

*Primary Examiner* — Kara E Geisel
*Assistant Examiner* — Jarreas C Underwood
(74) *Attorney, Agent, or Firm* — Schmeiser, Olsen & Watts LLP

(57) ABSTRACT

The invention provides differential refractive index detectors and methods for the use of differential refractive index detectors. In an exemplary embodiment, a differential refractive index detector includes a flow cell body having a proximal end, a distal end, and a flow axis extending between the proximal and the distal end. The flow cell body (Continued)

includes a first chamber and a second chamber and the fluid conduits coupled to the flow cell body can be tapered to reduce dispersion.

9 Claims, 7 Drawing Sheets

(56) References Cited

U.S. PATENT DOCUMENTS

| | | | | |
|---|---|---|---|---|
| 3,386,332 A * | 6/1968 | Watson | ............... | G01N 21/4133 356/130 |
| 3,612,697 A * | 10/1971 | Nebe | ................. | G01N 21/4133 250/576 |
| 3,950,104 A * | 4/1976 | Munk | .................... | G01N 21/41 356/128 |
| 4,229,105 A * | 10/1980 | Silverbage | ............. | G01N 21/45 356/130 |
| 5,398,110 A * | 3/1995 | Kitaoka | ............. | G01N 21/4133 356/130 |
| 5,608,517 A * | 3/1997 | Munk | ................. | G01N 21/0303 356/246 |
| 5,900,152 A * | 5/1999 | Janik | ...................... | G01N 30/74 210/198.2 |
| 6,094,262 A * | 7/2000 | Almeida | ............ | G01N 21/4133 356/130 |
| 6,295,125 B1 * | 9/2001 | Tokieda | ............. | G01N 21/4133 356/130 |
| 6,975,392 B2 * | 12/2005 | Larkin | ............... | G01N 21/4133 356/128 |
| 7,283,221 B2 * | 10/2007 | Larkin | ............... | G01N 21/4133 356/130 |
| 7,320,775 B2 * | 1/2008 | Kochy | ............... | G01N 15/1456 204/601 |
| 7,551,270 B2 * | 6/2009 | Nakamura | ............. | G01N 21/05 210/198.2 |
| 7,724,356 B2 * | 5/2010 | Tokieda | ............. | G01N 21/0303 356/128 |
| 8,134,705 B2 * | 3/2012 | Kaduchak | .......... | G01N 15/1404 356/337 |
| 8,196,455 B2 * | 6/2012 | Anderson | ............ | G01N 29/022 73/61.49 |
| 8,292,083 B2 * | 10/2012 | Varghese | ............. | B03C 1/0332 209/215 |
| 2004/0110208 A1 | 6/2004 | Chan et al. | | |
| 2007/0076192 A1 * | 4/2007 | Nakamura | ......... | G01N 21/4133 356/131 |

OTHER PUBLICATIONS

Examination Report in United Kingdom Patent Application No. GB1515755.5, dated Jul. 6, 2017; 6 pages.
Examination Report in UK Patent Application No. GB1515755.5, dated Dec. 20, 2017; 3 pages.
Examination Report in UK Patent Application No. GB1515755.5, dated Mar. 14, 2018; 3 pages.

* cited by examiner

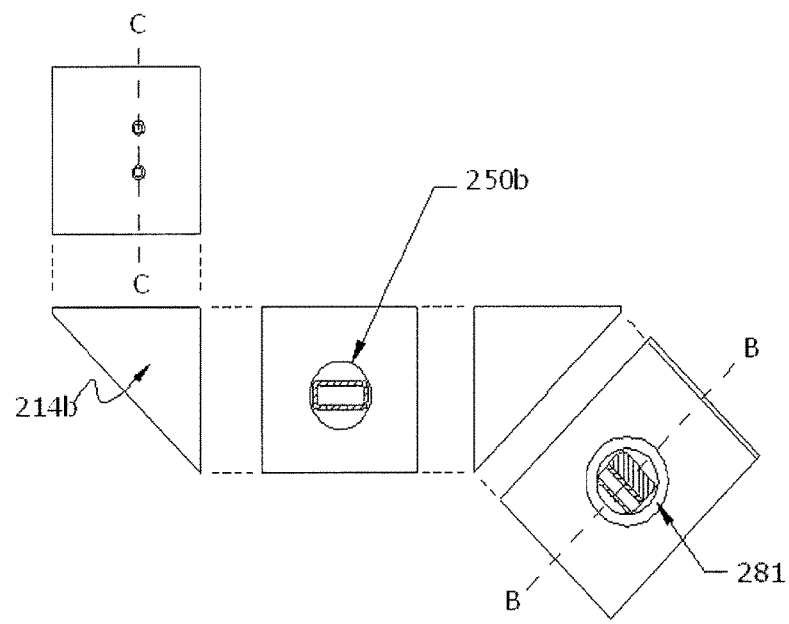
FIG. 6A
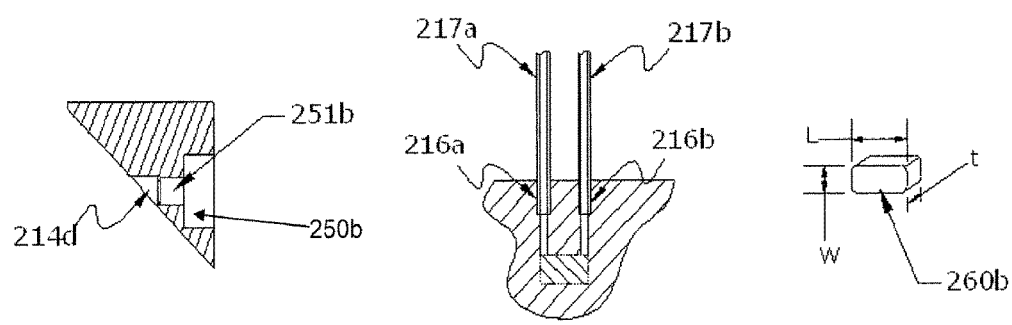
FIG. 6B  FIG. 6C  FIG. 6D

SYSTEMS AND METHODS FOR REFRACTIVE INDEX DETECTION

RELATED APPLICATIONS

This application claims priority to and benefit of U.S. Provisional Patent Application No. 61/819,811 entitled "Systems, Methods and Devices for Refractive Index Detection," filed May 6, 2013 and U.S. Provisional Patent Application No. 61/789,098 entitled "Systems, Methods and Devices for Refractive Index Detection," filed Mar. 15, 2013. The contents and teachings of each of these applications are hereby expressly incorporated herein by reference in their entirety.

FIELD OF THE INVENTION

The present invention generally relates to refractive index detection, and in particular, systems, methods and devices for measuring refractive index differences with low fluidic dispersion.

BACKGROUND

The measurement of the refractive index or RI of a fluid such as a gas or liquid has widespread applications across many industries. RI is a property of a fluid which characterizes its response to an externally applied electromagnetic radiation field. Different substances respond to the same field to an extent dependent upon the specific material and it is this varying response which forms the basis for both quantifying a given material and distinguishing it from another. Generally though, the qualitative aspects of an RI measurement are less sought after than its appeal as a quantitative tool since many substances, such as sugars, are less amenable to other forms of analysis such as UV absorbance detection (i.e., they lack of strong UV chromophore) or fluorescence. RI is sometimes referred to as a universal detector since so many substances will exhibit an RI response. In particular, an RI detector preceded by a separation means, such as a liquid chromatograph, will yield responses for virtually all substances. In this measurement mode, a sample containing one or more analytes is injected onto a chromatographic column. Subsequent continuous flow of a clean mobile phase through the column leads to a separation in time of the individual analytes. These analytes elute or exit from the column as individual peaks having a characteristic volume and retention time reflective of the analyte and column packing material. The peak is transported from the column to the RI detector, which produces a response proportional to analyte concentration. Since each peak contains the original quantity of analyte dissolved within the mobile phase, the more compact or narrow the volume of the peak, the larger the RI response will be for the same injected mass. Compact peaks are characteristic of minimal dispersion during transit of the analyte peak from the column to the detector. The process whereby the peak exiting the column is broadened during transport to a downstream detector is generally referred to as post-column dispersion.

Proper management of post-column dispersion can allow the volumetric scale of the separation to be decreased, which can yield meaningful gains in signal enhancement for many detection methods, including concentration sensitive analyzers such as differential RI detectors. Peak volumes decrease in proportion to the cross-sectional area of the column. Thus, for two columns whose diameters differ by a factor of two, the peak volume for the smaller ID column is expected to be four times smaller and therefore for the same mass injected, the concentration should be four times larger. There are other important advantages in going to smaller scale separations. For example, reduced solvent consumption is an advantage for applications that employ expensive mobile phases, which are common in RI detection.

Large scale chromatographic systems can be categorized as those employing separation columns with internal diameters (IDs) greater than about 4 mm, small scale columns with IDs in the range of about 1-4 mm, and capillary scale systems with IDs less than about 1 mm. Chromatographic theory can predict the peak volume of a retained analyte and it is this volume which serves as a guide in judging the effects of post-column dispersion. For the preceding range of columns, packed with conventional particles, typical peak volumes for early eluting analytes ($k'=2$) are shown in Table 1.

TABLE 1

| Column ID, mm | Column Length, mm | Particle Size, microns | Peak Volume (4.4%), µL | Optimum Flow Rate, ml/min | Time, min, for 1 Column Volume |
|---|---|---|---|---|---|
| 4.6 | 150 | 3.5 | 180 | 0.56 | 2.94 |
| 3.0 | 100 | 1.7 | 44 | 0.49 | 0.95 |
| 0.5 | 100 | 1.7 | 1.2 | 0.014 | 0.95 |

In practice, system parameters such as flow rate, operating pressure, etc. will be affected by the column choice. Relative to a large scale separation, the same application can be carried out with a small scale system in a manner that yields benefits both in time and reduced solvent consumption. As peak volumes for small scale systems are smaller, tighter constraints are placed on controlling sources of post-column dispersion. Accordingly, there is a need for low dispersion differential refractometers intended for separations conducted on small scale systems.

A broad range of RI detectors coupled to a separation system have been described in the art. For example U.S. Pat. No. 3,674,373 describes a heat exchanger for a differential refractometer. As is well-known, the temperature coefficient of the refractive index of most fluids is such that poor thermal control can lead to unwanted detector responses which are many times larger than the signal of interest. The '373 patent discloses tubing with inner diameters in the range of 0.02" to 0.04" with lengths of up to 12". These tubing dimensions correspond to post-column volumes from 60 µL, to 160 µL, which are unsuitable for small scale separations. U.S. Pat. No. 3,999,856 describes a diffractometric refractometer which measures a phase shift between a probe beam which has passed through a reference and sample flow cell chamber. Flow cell volumes as small as 2 µL, are discussed, but such small cells generally have short mechanical pathlengths, which can lead to limitations when attempting to measure both very small and large refractive index differences. The '856 patent does not disclose detector volumes between the column and flow cell or thermal management of the sample or reference streams.

Many techniques have been described in the art for measuring refractive index difference based upon a phase shift of light which has traveled through reference and sample fluid cells and which is then recombined in a plane distant from the cell. These techniques, broadly classified as interferometric methods, can be carried out with low volume flow cells but still require low pre-cell fluidic volumes and good thermal management to enable accurate RI differences.

U.S. Pat. No. 4,952,055 describes a beam displacement technique carried out in a capillary-based flow cell. While low volume cells are feasible, a setup method is described that requires alignment of the probe beam to the flow cell at an angle based upon the refractive index of the cell material (glass) and the sample fluid. Thus, measuring RI differences over a large range of absolute RI (e.g., from 1.30 to 1.60 RI units) as would be necessary in a general purpose RI detector, would necessitate optical realignments which could negatively impact instrument performance. Other techniques, such as those employing evanescent sensing (e.g., as disclosed in U.S. Pat. No. 5,311,274) may also be realized in low volume configurations but have limited range due to the dependence upon the refractive index of the light-carrying material.

U.S. Pat. No. 5,606,412 and U.S. Pat. No. 5,900,152 describe apparatus for modifying flow profiles within a non-circular flow cell by generally directing this flow towards the interior side surfaces of the cells. The apparatus of these patents refer to flow cells having volumes in the range of about 7 to 50 µL, which are more suitable for large scale chromatography.

Accordingly, there remains a need for robust, wide-ranging, and sensitive differential RI detectors exhibiting low dispersion.

SUMMARY

A robust, wide-ranging, and sensitive differential RI detector exhibiting low dispersion can be achieved by reducing the volume of the detector system, e.g., by minimizing the length of fluidic paths within the detector, subject to thermal control of the incoming fluid stream and spatially-tailored injection of the fluid into the sample chamber. Flow cells according to embodiments of the present invention can also be capable of operation at high pressures.

One aspect of the invention provides a differential refractive index detector that includes a flow cell body having a proximal end, a distal end, and a flow axis extending between the proximal and the distal end. The flow cell body includes a first chamber and a second chamber. In some embodiments, the first chamber can have a volume less than a volume of the second chamber. In an exemplary embodiment, at least one of the first chamber and the second chamber can have a volume in the range of about 2 µL to about 5 µL.

The flow cell body also includes a first inflow port configured to allow a fluid to flow into the first chamber, a first outflow port configured to allow fluid flow out of the first chamber, a second inflow port configured to allow fluid flow into the second chamber, and a second outflow port configured to allow fluid flow out of second chamber. At least one of the first and second inflow ports can be configured to provide fluid flow in a direction parallel to the flow axis of the flow cell body. In exemplary embodiments, at least one of the first and second inflow ports can be disposed at the proximal end of the flow cell. In some embodiments, at least one of the first and second outflow ports can be disposed at the distal end of the flow cell.

The differential refractive index detector can also include an inflow conduit coupled to one of the first inflow port and the second inflow port. The inflow conduit can have a proximal end, a distal end, and a flow axis extending between the proximal end and the distal end. In some embodiments, the inflow conduit can be tapered from a first diameter at the proximal end to a larger second diameter at the distal end. For example, an inner diameter of the inflow conduit at the distal end can be greater than an inner diameter of the fluid conduit at the proximal end. For example, the inner diameter of the inflow conduit at the distal end being greater than the inner diameter of the inflow conduit at the proximal end can provide a taper angle of the inflow conduit in the range of about 8° to about 20°.

The differential refractive index detector can also include an outflow conduit coupled to one of the first outflow port and the second outflow port. The outflow conduit can have a proximal end, a distal end, and a flow axis extending between the proximal end and the distal end. In some embodiments, the outflow conduit can be tapered from a first diameter at the proximal end to a smaller second diameter at the distal end. For example, an inner diameter of the outflow conduit at the proximal end can be greater than an inner diameter of the outflow conduit at the distal end. For example, the inner diameter of the outflow conduit at the proximal end being greater than the inner diameter of the outflow conduit at the distal end can provide a taper angle of the outflow conduit in the range of about 8° to about 20°.

The flow cell of the refractive index detector can be formed from various materials. For example, at least a portion of the flow cell body can be formed of clear quartz.

Another aspect of the invention provides a differential refractive index detector that includes a flow cell body having a proximal end, a distal end, and a flow axis extending between the proximal and the distal end, the flow cell comprising a first chamber and a second chamber. Each of the first chamber and the second chamber can have an inner surface extending substantially parallel to the flow axis of the flow cell body. In an exemplary embodiment, the flow cell body can include a first assembly and a second assembly, the first assembly defining the first chamber and the second assembly defining the second chamber. The flow cell body can also include at least one window configured to prevent fluid communication between the first chamber and the second chamber, the at least one window configured to transmit light between the first chamber and the second chamber. For example, the at least one window can be formed of clear quartz.

In some embodiments, at least a portion of the inner surface of at least one of the first chamber and the second chamber can be shaped to minimize sharp corners extending along the flow axis. For example, a cross-sectional profile of at least one of the first chamber and the second chamber taken perpendicular to the flow axis of the flow cell body can include at least one curved portion.

The flow cell body can also include a first inflow port configured to allow a fluid to flow into the first chamber, a first outflow port configured to allow fluid flow out of the first chamber, a second inflow port configured to allow fluid flow into the second chamber, and a second outflow port configured to allow fluid flow out of second chamber. At least one of the first and second inflow ports can be configured to provide fluid flow in a direction parallel to the flow axis of the flow cell body. In exemplary embodiments, at least one of the first and second inflow ports can be disposed at the proximal end of the flow cell. In some embodiments, at least one of the first and second outflow ports can be disposed at the distal end of the flow cell.

The differential refractive index detector can also include an inflow conduit coupled to one of the first inflow port and the second inflow port. The inflow conduit can have a proximal end, a distal end, and a flow axis extending between the proximal end and the distal end. In some embodiments, the inflow conduit can be tapered from a first diameter at the proximal end to a larger second diameter at the distal end. For example, an inner diameter of the inflow conduit at the distal end can be greater than an inner diameter of the fluid conduit at the proximal end. For example, the inner diameter of the inflow conduit at the distal end being greater than the inner diameter of the inflow conduit at the proximal end can provide a taper angle of the inflow conduit in the range of about 8° to about 20°.

The differential refractive index detector can also include an outflow conduit coupled to one of the first outflow port and the second outflow port. The outflow conduit can have a proximal end, a distal end, and a flow axis extending between the proximal end and the distal end. In some embodiments, the outflow conduit can be tapered from a first diameter at the proximal end to a smaller second diameter at the distal end. For example, an inner diameter of the outflow conduit at the proximal end can be greater than an inner diameter of the outflow conduit at the distal end. For example, the inner diameter of the outflow conduit at the proximal end being greater than the inner diameter of the outflow conduit at the distal end can provide a taper angle of the outflow conduit in the range of about 8° to about 20°.

BRIEF DESCRIPTION OF THE DRAWINGS

The invention will be more fully understood from the following detailed description taken in conjunction with the accompanying drawings, in which:

FIG. 6A illustrates the reference chamber of the flow cell assembly of FIG. 5A according to an embodiment of the present invention;

FIG. 6B is a sectional view of the reference chamber of FIG. 6A taken along line B-B;

FIG. 6C is a sectional view of the reference chamber of FIG. 6A taken along line C-C;

FIG. 6D illustrates a window of the reference chamber of FIG. 6A according to an embodiment of the present invention;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
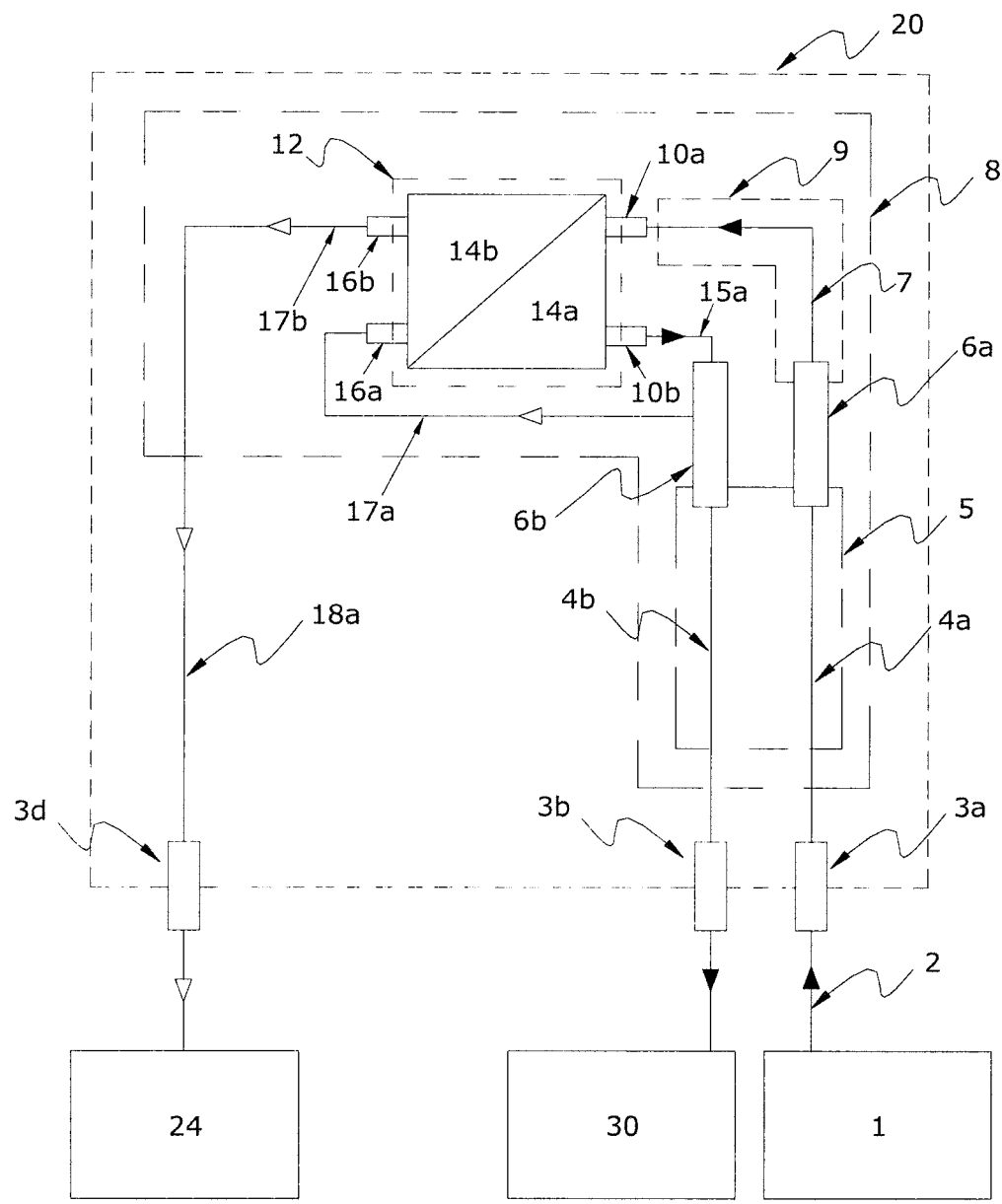
FIG. 1 illustrates a schematic layout of a differential RI detector coupled to a separation system, according to an embodiment of the present invention.

FIG. 1 illustrates an exemplary separation system including a differential RI detector. The separation system includes a separation unit 1. The separation unit 1 can include various modules. For example, the separation unit 1 can include modules such as a sample organizer, a pump for delivering fluid(s), a sample injector, a separation column, a column manager, and a central control unit such as a computer on which software is installed for directing the overall separation. The separation system can also include an RI detector 20. The RI detector 20 can include various fluidic and thermal conditioning or control means, discussed in more detail below. The RI detector 20 can also include an optical sensing system configured to quantify the difference in refractive indices of fluids contained within separation chambers of a flow cell 12. As discussed in more detail below, the detector 20 has two primary modes of operation, which are referred to herein as a purge mode and a normal mode.

When operating in purge mode, the separation unit 1 delivers a reference fluid along a path 2 to a detector inlet 3a. In purge mode, a valve in outflow unit 30 is closed, which forces flow along the path between the detector inlet 3a and the flow cell inlet port 10a, through the sample chamber 14a of the flow cell 12, then into the reference chamber 14b of flow cell 12, then exiting the reference chamber along conduits 17b and 18a, and finally passing into outflow unit 24 from which the fluid may be diverted either to waste or a recycling container. After a completed purge operation in purge mode, the fluid composition within the chambers 14a, 14b of the flow cell 12 is the same. During this period, i.e., when the fluid composition of the chambers 14a, 14b of the flow cell are identical, the optical sensing system can then be used to collect a calibration signal. The calibration data can include a detector output signal and can be stored in a digital memory location.

When operating in normal mode, a test sample is injected onto the column within test unit 1 and a separation of this sample into one or more analytes commences as the reference fluid is flowed through the column at constant flow rate. The eluant from the column is transported to the RI detector 20 via fluid conduit 2. In exemplary embodiments, the fluid conduit 2 can be sized to minimize dispersion between the outlet of the column and the connection at the detector 3a, which can also be of a low dispersion type. In some embodiments, the temperature of the interior of the detector 20 can be controlled by a master control unit, not shown. In normal mode, a valve in outflow unit 30 is opened resulting in an active fluid path along conduit 4b and into unit outflow unit 30 through connector 3b. The outflow unit 30 may be configured to divert the flow either to waste or a recycling container. In normal mode, there is no flow along conduit 17a into the reference chamber 14b or exit from the reference chamber 14b along conduit 18a. However, a hydraulic connection still exists between these flow paths, which can mitigate unwanted detector responses that can result from pressure variations associated with the separation unit 1, e.g., by maintaining the two chambers of the flow cell 12 at the same pressure. During operation in the normal mode, the detector output signal is collected. The detector output signal is processed to remove the calibration signal recorded in purge mode and scaled by known factors to yield a detector output value representing the refractive index difference between the analyte contained within the sample chamber 14a and the reference fluid within chamber 14b of the flow cell 12. Analyte concentration may be related to the refractive index difference through a separate calibration step. The record of the detector output signal versus time forms a chromatogram.

As discussed above, the temperature of the interior of the detector 20 can be controlled, e.g., by a master temperature control unit. In some embodiments, the incoming test fluid can be thermally conditioned. For example, a first internal thermal conditioning module 5 can adjust the temperature of the incoming fluid within conduit 4a to the temperature of the outgoing fluid flow through conduit 4b. In exemplary embodiments, thermal conditioning module 5 can be a countercurrent heat exchanger. The fluidic volume of conduit 4a within the first internal conditioning module 5 can be reduced to a sufficiently small value while providing high efficiency so that its contribution to overall peak dispersion can be minimized for a broad range of flow rates and fluid viscosities. In some embodiments, the detector 20 can include a second thermal conditioning unit 9. The second thermal conditioning unit 9 can be a heat sink whose absolute temperature is tightly regulated by a master heater control unit. Flow cell 12 and the fluidic inlet and outlet ports 10a, 10b, 16a, 16b can be attached to the second thermal conditioning unit 9 through standard mechanical means, such as by screws, press fits, welding, brazing, etc. Further thermal shielding can be provided by an enclosure, which provides further isolation from other components such as circuit cards, etc. within the interior of 20.

One skilled in the art will appreciate that an analyte's post-column peak shape is typically determined by the dispersive properties of the fluid path from the separation unit through the detector, e.g., from 1 to 15a in FIG. 1. Low dispersion tubing and connectors, e.g., conduit 2 and connector 3a in FIG. 1, are well known and readily available. Low dispersion tubing can be characterized as having small lumen diameters and smooth internal surfaces. Exemplary low dispersion connectors include commercially available zero dead volume unions.

The dispersive properties of the fluid path from the separation unit through the detector are also affected by the length and volume of the various portions of that fluid path. For example, on the fluid path from 3a to 10b in FIG. 1, for a volume of conduit 4a less than about 20 µL, the heat exchanger efficiency of 5 can be maintained at very high levels, e.g., in excess of 80%, for flow rates as large as 2 ml/min. The efficiency of heat exchanger 5 can also be maintained for flow rates as large as 2 mL/min for volumes of conduit 4a less than about 10 µL, and as small as about 2 µL. The volume of conduit 7 within thermal conditioning unit 9 can also be reduced to less than about 10 µL, and in some embodiments, less than about 5 µL, and still provide the level of thermal stabilization needed for low noise. For example a differential RI detector employing the low volume thermal conditioning units described herein can achieve noise levels comparable to an RI detector with a thermal conditioning volume more than 10 times larger. In conjunction with the reduced tubing volumes, the flow pattern into 14a can also be spatially tailored, e.g., by internal tapering of the connection 10a, as discussed in more detail below.

Figure 2A:
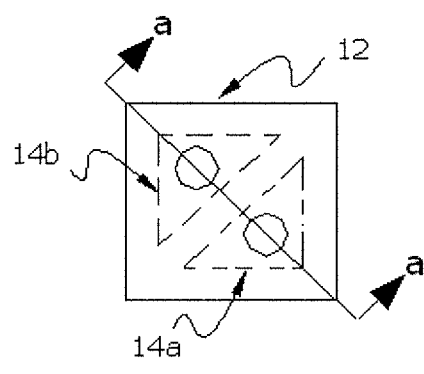
FIG. 2A illustrates a refractometer flow cell with prismatic sample and reference chambers.
Figure 2B:
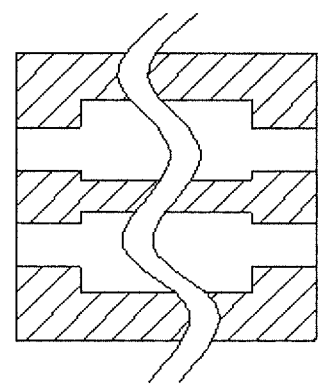
FIG. 2B is a sectional view of the flow cell of FIG. 2A taken along line a-a.

Flow through a conduit is influenced by several factors including the shape of the conduit. In exemplary flow cells, flow can be introduced into the cell axially. For example, FIGS. 2A and 2B illustrate a refractometer flow cell 12 that includes axial ports. However, axial ports can be insufficient to minimize all the effects of disturbances to flow profiles in fluid chambers having rectangular or triangular-shaped cross sections, e.g., as shown in FIGS. 2A and 2B.

Figures 3A, 3C:
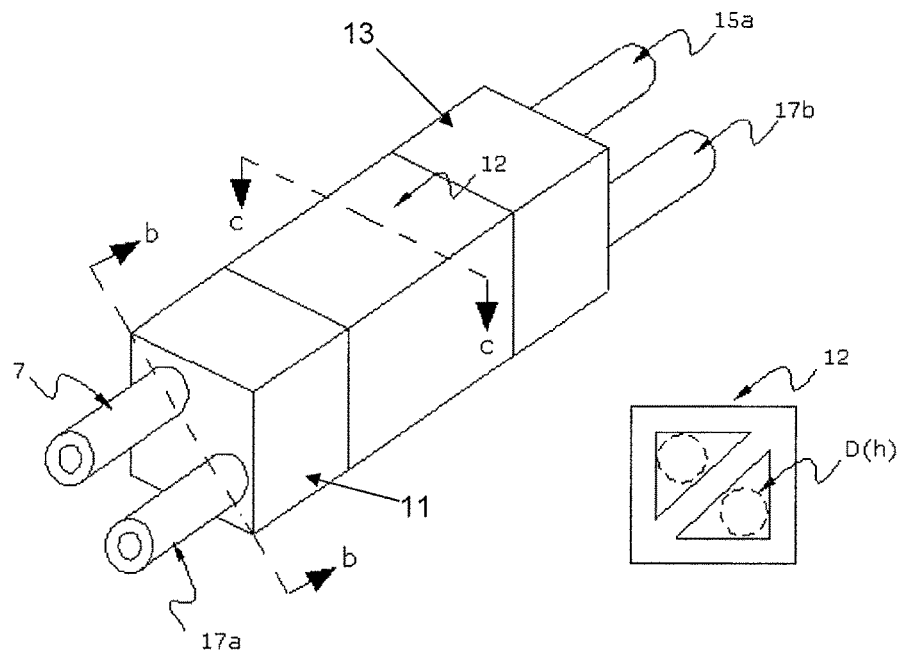
FIG. 3A illustrates a refractometer flow cell assembly according to one embodiment of the present invention.
FIG. 3C is a sectional view of the flow cell of FIG. 3A taken along line c-c.

Fluid ports having a tapered profile, coupled in some embodiments with appropriately small conduit volumes leading into the RI cell, can decrease dispersion to such a degree that differential RI detection can be carried out on small scale separations. FIG. 3A illustrates a flow cell according to one embodiment of the present invention. The sectional view of FIG. 3B depicts various connection details.

Figure 3B:
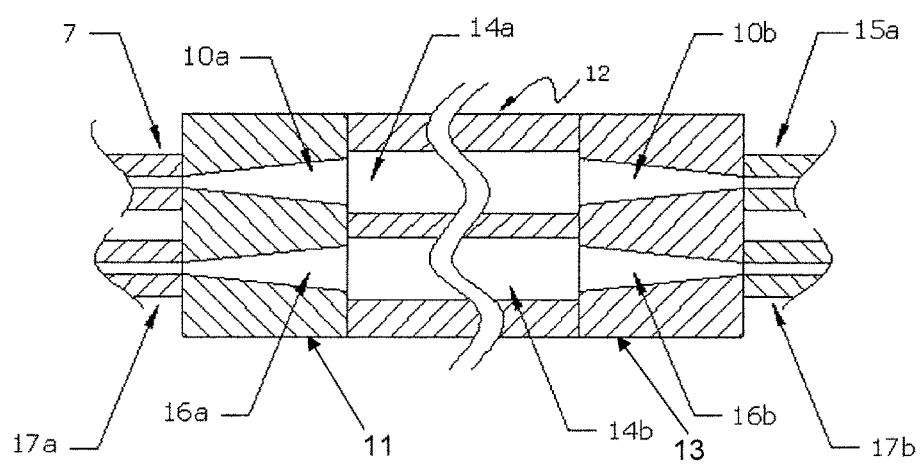
FIG. 3B is a sectional view of the flow cell of FIG. 3A taken along line b-b.

In the exemplary flow call of FIGS. 3A and 3B, a sample flows into the RI cell 12 through low volume, small bore conduit 7 before entering the sample chamber 14a. When the fluid from conduit 7 enters the chamber 14a there will be energy loss due to sudden expansion in the cross-sectional area of 14a. Such changes in cross-section can lead to unwanted effects such as flow reversal (eddies) arising from very low fluid velocities along the interior corners of the chamber. To mitigate the energy loss due to this sudden change in the hydraulic diameter between conduit 7 and prism compartment 14a, a taper of suitable angle is provided. The purpose of the taper is to allow for a gradual change in velocity and minimize the energy loss as the fluid enters the prism compartment, 14a. The taper angle can be selected to optimize transition in velocity, i.e., to promote a smooth and gradual velocity change. For example, the total taper angle can be in the range of about 8° to about 20°. In some embodiments, the taper angle can be in the range of about 8° to about 10° or about 10° to about 20°. For example, the taper angle can be about 8°, about 10°, or about 20°. In an exemplary embodiment, the hydraulic diameter of the outlet of the tapered section can be selected to match the largest diameter of an inscribed circle defined by the boundaries of the prism compartment, 14a, illustrated by D(h) in FIG. 3C.

In exemplary embodiments, the transition from conduit 7 into the sample chamber 14a can be provided by a connector 11 having a connector bore 10a, as shown in FIG. 3B. As noted above, tapering the connector bore 10a can reduce the fluid velocity and the resulting dispersion. Likewise, the transition from conduit 17a into the reference chamber 14b can be provided by a connector bore 16a in connector 11, which can also be tapered as discussed above. Similarly, the transition from the sample chamber 14a and the reference chamber 14b can be provided by a connector 13 having connector bores 10b and 16b, which can also be tapered. In other embodiments, the connector bores 10a, 10b, 16a, 16b may not be tapered. For example, under normal circumstances, there would be no need to employ tapered connectors, 16a, 16b for the reference chamber 14b because the fluid contained therein is substantially static. For example, connector bores 16a and 16b can have a straight bore that matches the inner diameter of fluid conduits 17a and 17b.

The conduits 7, 17a, 15a, and 17b can have an inner profile of elliptical or circular shape. In exemplary embodiments, the internal diameter of the fluid conduits, e.g., fluid conduits 7, 15a, 17a, and/or 17b can be less than or equal to about 0.011". For example, the internal diameter of these fluid conduits can be less than or equal to about 0.005", or in the range of about 0.005" to about 0.011". In exemplary embodiments, the flow cell chamber volume, i.e., the volume of the sample chamber or the reference chamber, can be less than or equal to about 5 µL. For example, the flow cell chamber volume can be in the range of about 2 µL to about 5 µL, or less than or equal to about 2 µL. In one embodiment, the flow cell sample chamber and reference chamber cross sections can be right triangles having equal side lengths of about 0.80 mm and the flow cell chambers can have a length of about 4.0 mm, resulting in flow cell chambers with an internal volume of about 1.3 µL. For such a flow cell, the largest diameter of an inscribed circle defined by the boundaries of the sample chamber 14a or the reference chamber 14b, illustrated by D(h) in FIG. 3C would be about 0.468 mm (0.0184").

Standard fastening means such as brazing or welding may be used to attach metal conduits to the taper sections, such as conduit 7 to taper section 10a. The cell 12 can be sealed to each connector assembly using compliant gaskets made from materials such as Teflon or PEEK. The gaskets may be in the form of flat sheets with suitable apertures or O-Rings to permit the unrestricted flow of fluids into and out of the respective chamber.

Figure 4:
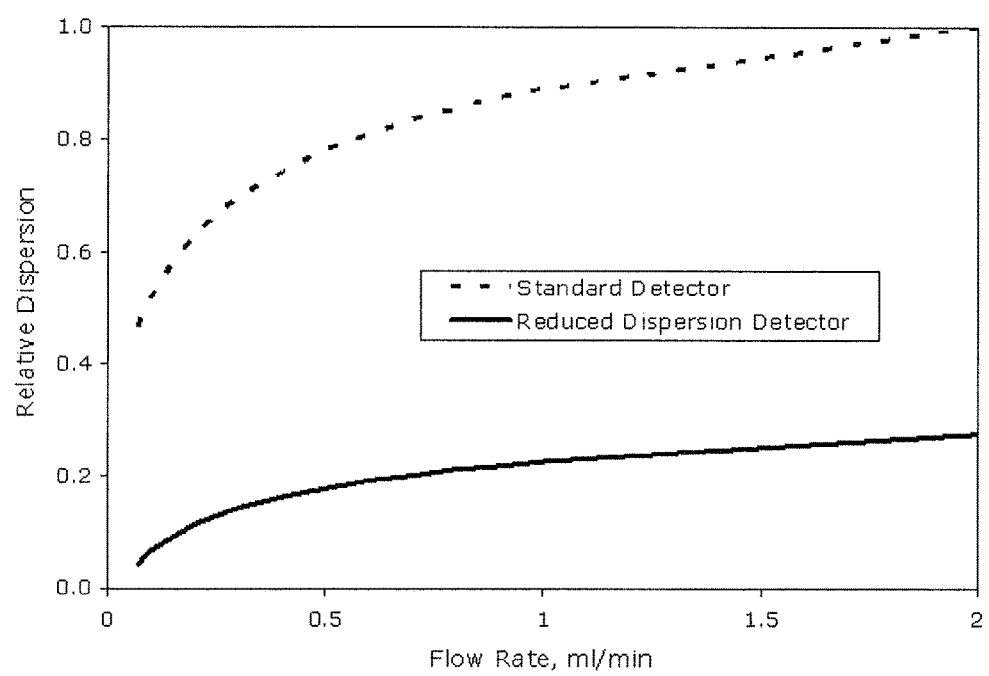
FIG. 4 is an exemplary plot of dispersion and flow rate for two differential RI detectors.

FIG. 4 is a plot of dispersion for a range of flow rates for a standard differential RI detector intended for large scale separation systems and a reduced dispersion detector according to embodiments of the present invention. As shown in FIG. 4, the dispersion of the standard detector is at least 4 times larger than reduced dispersion detectors according to the present invention for the region of optimum flow rate of the large and small scale separation columns from Table 1. The nearly 3 times speed benefit of going to a small column shown in Table 1 can also be achieved without any decrease in chromatographic efficiency using reduced dispersion detectors according to the present invention. As many chromatographic applications are not sample limited, the reduced dispersion may be further exploited by loading where practical the same mass on column as for the large system, which is expected to lead to an increase in peak heights of nearly 4-fold. Such an increase provides numerous advantages, such as lower limits of detection.

The differential refractometer flow cell 12 of FIG. 3 can be conventionally manufactured as an all-glass assembly, e.g., optically clear fused quartz. However, an all-glass assembly can limit the operational pressures of the cell to pressures less than about 100 psi. Beyond this pressure limit, certain elements of the flow cell are prone to fracture. In exemplary embodiments of the present invention, flow cells can be fabricated from discrete optically transmissive elements incorporated into a mechanical framework the overall pressure resistance of which is much higher. FIGS. 5A to 7B depict the elements of such an assembly. The flow cell assembly of FIGS. 5A to 7B can provide low dispersion and withstand high pressures, e.g., greater than about 100 psi. The flow cell assembly of FIGS. 5A to 7B, discussed in more detail below, can function equally well across both large and small scale separations and can be particularly advantageous for small scale separations.

Figure 5A:
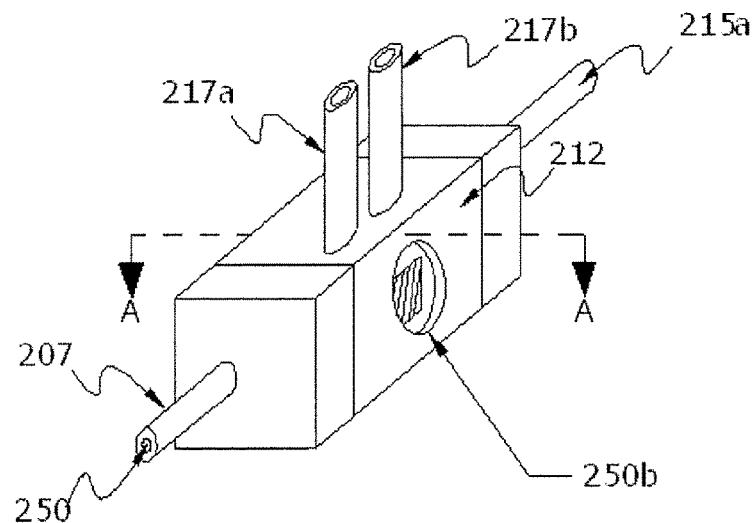
FIG. 5A illustrates a refractometer flow cell assembly constructed to withstand high operating pressures according to an embodiment of the present invention.

The flow cell assembly of FIG. 5A is similar to that illustrated in FIG. 3A, with differences arising from the configuration of the flow cell 212. Sample flow enters the differential RI cell through conduit 207 whose lumen diameter 250 is selected according to desired dispersion properties, as discussed above. The dimensional features of the exit conduit 215a from this chamber are also chosen accordingly. As discussed above, the input conduit 217a and exit conduit 217b from the reference chamber are generally non-critical with respect to analyte peak dispersion. The fluid conduits 217a and 217b are shown in the exemplary embodiment illustrated in FIG. 5A entering perpendicular to the sample conduits 207 and 215a. In other embodiments, the fluid conduits 217a and 217b can enter the flow cell parallel to the sample conduits 207 and 215a.

Figure 5B:
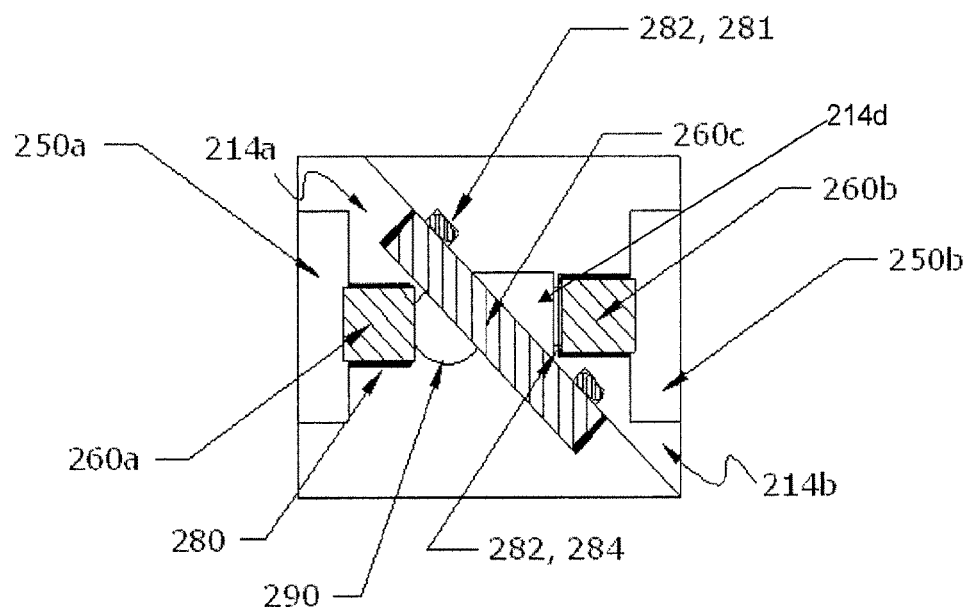
FIG. 5B is a sectional view of the flow cell of FIG. 5A taken along line A-A.

As shown in FIG. 5B, the flow cell prism assembly 212 includes two parts, defined by discrete assemblies 214a and 214b. Assembly 214a includes sample chamber 290. Assembly 214b includes reference chamber 214d. These assemblies may be joined in well-known manners such as by screws, clamps or other fasteners, not shown. The main joint between 214a and 214b includes an O-ring seal formed by O-ring 282 and a corresponding groove 281 in 214b. Optically transparent windows 260a, 260b, 260c provide for passage of the optical beam which interrogates the refractive index difference between the sample and reference fluids. The windows 260a, 260b, 260c also confine the respective fluids within each chamber by only permitting flow through the corresponding inlet and outlet conduits. Optical window 260c prevents the two fluids from directly exchanging, while windows 260a and 260b prevent leakage from within each chamber outside the cell 212. Windows 260a and 260b can be sealed to their respective machined (or molded) assemblies by edge seals 280 or by sheet-like gaskets 282 interposed between the respective window and its receiving surface 284.

In some embodiments, the flow cell 212 can include counterbore features 250a and 250b. The dimensions of the counterbore features 250a and 250b are chosen in accordance with the size of optical elements coupled to the flow cell. For example, the dimensions of the counterbore features 250a and 250b can be used to register masks which define a precise size of the optical beam passing through 212. In other examples, the counterbore features 250a and 250b can accommodate clamps or other retaining mechanisms to maintain the windows 260a and 260b in their respective recesses.

In exemplary embodiments, the sample chamber 290 can be formed by a circular or elliptical bore provided through the long axis of the assembly 214a. After machining to accommodate windows 260a and 260c, the circular bore 290 can yield a chamber profile in which sharp corners have been substantially eliminated. For example, a cross-sectional profile of sample chamber 290 taken perpendicular to the flow axis of the flow cell body can include at least one curved portion. The resulting chamber profile provides numerous advantages, such as more uniform flow profiles, which can lead to improved dispersion properties. In some cases, a portion of the bore 290 may not be interrogated by the optical beam. However, the improved flow profile can yield an overall reduction in peak dispersion. In some embodiments, the reference chamber dimensions can be increased relative to the dimensions of the sample chamber. In some embodiments, the cross-sectional profile of the reference chamber within the reference assembly 214b can also be elliptical or circular. In exemplary embodiments, the flow cell chamber volume, i.e., the volume of the sample chamber or the reference chamber, can be less than or equal to about 5 µL. For example, the flow cell chamber volume can be in the range of about 2 µL to about 5 µL, or less than or equal to about 2 µL.

Figure 7A:
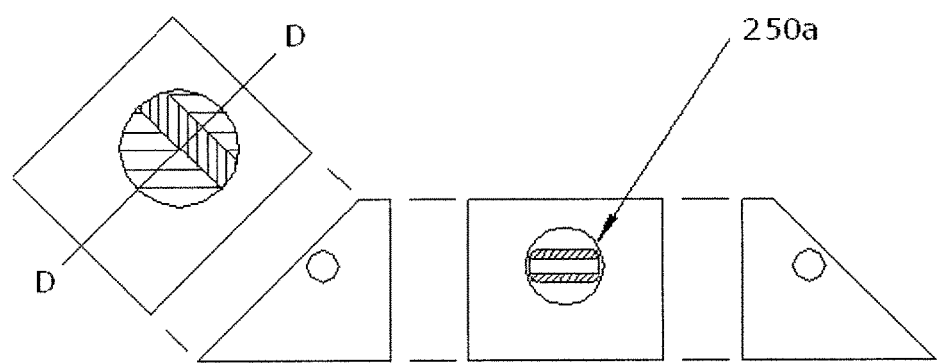
FIG. 7A illustrates the sample chamber of the flow cell assembly of FIG. 5A according to an embodiment of the present invention.
Figure 7B:
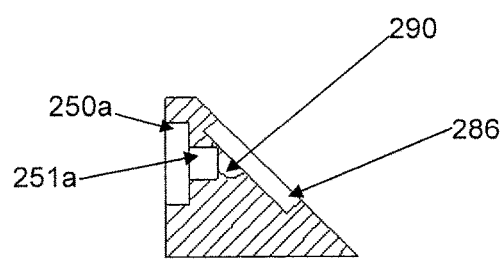
FIG. 7B is a sectional view of the sample chamber of FIG. 7A taken along line D-D.

FIGS. 6A to 6D illustrate reference assembly 214b in greater detail showing features associated with the various faces. Fluid conduits 217a and 217b can be attached to 214b via welding or other techniques. For example, the distal ends 216a and 216b of the fluid conduits 217a and 217b can be inserted into corresponding recesses in the outer surface of assembly 214b. The window 260b can be received in a cavity 251b, shown in FIG. 6B. The length L, width W and thickness t of window 260b illustrated in FIG. 6D can be chosen according to well-known engineering formulas based upon the desired pressure rating for the cell, window material, and sealing stresses. FIGS. 7A-7B illustrate the sample assembly 214a in greater detail showing features associated with the various faces. For clarity, the conduit 207 is omitted from FIG. 7A. FIG. 7B illustrates a sectional view taken along line D-D in FIG. 7A. The window 260a can be received in a cavity 251a, shown in FIG. 7B. The window 260c can be received in cavity 286, shown in FIG. 7B.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A differential refractive index detector, comprising:
    a flow cell body having a proximal end, a distal end, and a flow axis extending between the proximal and the distal end, the flow cell body comprising a first chamber and a second chamber;
    the flow cell body further comprising a first inflow port configured to allow fluid to flow into the first chamber, a first outflow port configured to allow fluid flow out of the first chamber, a second inflow port configured to allow fluid flow into the second chamber, and a second outflow port configured to allow fluid flow out of second chamber,
wherein at least one of the first and second inflow ports is configured to provide fluid flow in a direction parallel to the flow axis of the flow cell body and to reduce at least a portion of an effect of disturbance to a flow profile in at least one of the first and second chambers; and
    an inflow conduit shaped to reduce energy loss, the inflow conduit coupled to one of the first inflow port and the second inflow port, the inflow conduit having a proximal end, a distal end, and a flow axis extending between the proximal end and the distal end, an inner diameter of the inflow conduit at the distal end being greater than an inner diameter of the inflow conduit at the proximal end.

2. The differential refractive index detector of claim 1, wherein at least one of the first and second inflow ports is disposed at the proximal end of the flow cell.

3. The differential refractive index detector of claim 1, wherein at least one of the first and second outflow ports is disposed at the distal end of the flow cell.

4. The differential refractive index detector of claim 1, wherein the inner diameter of the inflow conduit at the distal end being greater than the inner diameter of the inflow conduit at the proximal end provides a taper angle of the inflow conduit in the range of about 8° to about 20°.

5. The differential refractive index detector of claim 1, further comprising:
    an outflow conduit coupled to one of the first outflow port and the second outflow port, the fluid conduit having a proximal end, a distal end, and a flow axis extending between the proximal end and the distal end, an inner diameter of the outflow conduit at the proximal end being greater than an inner diameter of the outflow conduit at the distal end.

6. The differential refractive index detector of claim 5, wherein the inner diameter of the outflow conduit at the proximal end being greater than the inner diameter of the outflow conduit at the distal end provides a taper angle of the outflow conduit in the range of about 8° to about 20°.

7. The differential refractive index detector of claim 1, wherein the first chamber has a volume less than a volume of the second chamber.

8. The differential refractive index detector of claim 1, wherein at least one of the first chamber and the second chamber has a volume in the range of about 2 µL to about 5 µL.

9. The differential refractive index detector of claim 1, wherein at least a portion of the flow cell body is formed of clear quartz.

* * * * *